Figure 1:
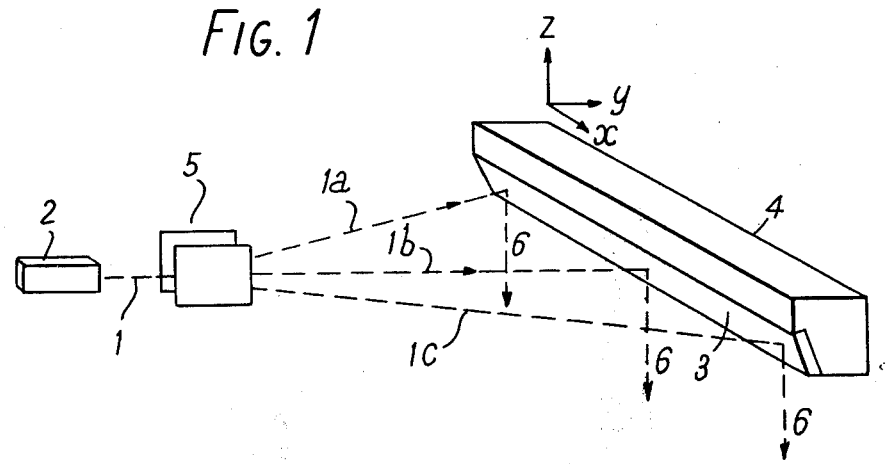

United States Patent [19]

Mayo

[11] 4,002,917
[45] Jan. 11, 1977

[54] SOURCES OF X-RADIATION
[75] Inventor: Bernard Joseph Mayo, Beaconsfield, England
[73] Assignee: EMI Limited, Hayes, England
[22] Filed: Aug. 27, 1975
[21] Appl. No.: 608,276
[30] Foreign Application Priority Data
Aug. 28, 1974 United Kingdom ............ 37563/74
[52] U.S. Cl. ........................... 250/445 T; 250/403; 250/360
[51] Int. Cl.² ....................................... G03B 41/16
[58] Field of Search ........ 250/416 TV, 445 T, 439, 250/444, 445 R, 446, 447, 448, 449, 450, 523, 402, 358, 359, 360

[56] References Cited
UNITED STATES PATENTS 2,667,585  1/1954  Gradstein .................. 250/416 TV
3,778,614  12/1973  Hounsfield .................... 250/445 T

*Primary Examiner*—Craig E. Church
*Attorney, Agent, or Firm*—Fleit & Jacobson

[57] ABSTRACT

Radiological apparatus is described for producing a representation of the variation of absorption coefficient with position over at least one planar slice taken cross-sectionally through a body under examination. The source of radiation comprises an X-ray tube having a target with an extended dimension in a direction substantially perpendicular to the plane of the aforementioned planar slice, and means is provided for scanning the electron beam of the tube along the extended dimension of the target so as to scan the X-radiation relative to the body in said direction.

5 Claims, 4 Drawing Figures

SOURCES OF X-RADIATION

The present invention relates to sources of X-radiation and is especially, though not exclusively, related to X-ray sources for the use with scanning radiological apparatus.

In U.S. Pat. No. 3,778,614 there is disclosed scanning radiological apparatus which is capable of producing a representation of the absorption coefficient (with respect to the radiation used) at each of a plurality of locations distributed over a planar slice of a body under examination. In order to permit the production of such a representation, one example of the apparatus disclosed in the aforementioned Patent Specification employs a single pencil-like beam of X-radiation which is produced by a suitable source and which, after passing through the body in the plane of the required slice, is detected by means of a suitably collimated detector. The source and the detector are then scanned relative to the body so that the pencil beam of radiation traverses a succession of different paths through the body, all of the paths being in the plane of the said slice, and the detector provides output signals which are indicative of the absorption suffered by the radiation on traversing each path through the body. These output signals are processed to evaluate the aforementioned absorption coefficients, and the required representation is then produced.

In said example of the apparatus, the scanning of the source and detector relative to the body involves physical movement of both elements and they are caused to perform alternate linear traverses and rotational steps, the latter being executed about an axis passing through the body perpendicularly to the said slice.

When the speed at which the output signals are acquired is important, the kind of scanning procedure described in the last preceding paragraph is not entirely satisfactory. Alternative scanning techniques have been proposed, for example that in U.S. Pat. No. 3,946,234 in which the single beam is replaced by a fan-shaped set of beams emanating from a point source and detector is provided for each beam of the set. The source and the detectors are both still required to execute translational and rotational scans, but the scanning procedure is faster than the one previously described because the rotational movements can be through an angle commensurate with the angle subtended by the fan of beams, instead of the much smaller angle between two adjacent beams of the fan-shaped set which is the approximate angle of rotation required when a single beam is used.

However in accordance with this invention it has been realised that the scanning speed can be increased still further by avoiding altogether the use of a mechanically operated lateral scan. This is achieved by using an electrically scanned X-ray source (again of a fan-shaped set of beams) and a fixed bank of detectors which has a wider extent than is required to accommodate the fan-shaped set of beams in any one position of the electrically effected lateral scan. The rotational motion of the source and detectors is still required, of course, but since the lateral scanning is effected electrically it can be done so rapidly that there is no need for rotational motion to be executed in steps. The scanning requirement thus reduces to a rotational scan effected at a steady speed.

Instead of utilising the electrically effected scanning of the radiation to carry out the lateral scan, as described above, it could be used, for example in conjunction with an arrangement of the kind described in the aforementioned U.S. Pat. No. 3,946,234, to enable successive parallel slices of the body to be investigated without the need for re-locating or mechanically moving the patient or the scanning structure. This can be achieved, in accordance with the invention, by arranging for the electrical scanning of the tube to be performed in a direction at right angles to the plane of a slice, thereby shifting the radiation so that it can examine adjacent slice. In this case, the electrical scanning would not be continuous, but it would be effected in steps after each (say) 180° or 360° of rotational movement.

According to the invention, therefore, there is provided radiological apparatus including a source of X-radiation having a target electrode arranged to emit X-radiation in response to a beam of electrons impinging thereon, detector means for detecting the radiation after it has passed through a planar slice of a body, means for scanning the source and detector means relative to the body to permit radiation traversing a plurality of coplanar paths in said slice to be detected by said detector means, and deflection means for deflecting said beam of electrons in a direction substantially perpendicular to the plane of said paths to enable an adjacent slice of said body to be irradiated.

Figure 2A:
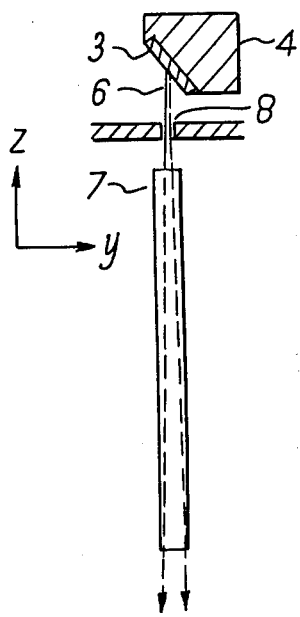
Figure 2B:
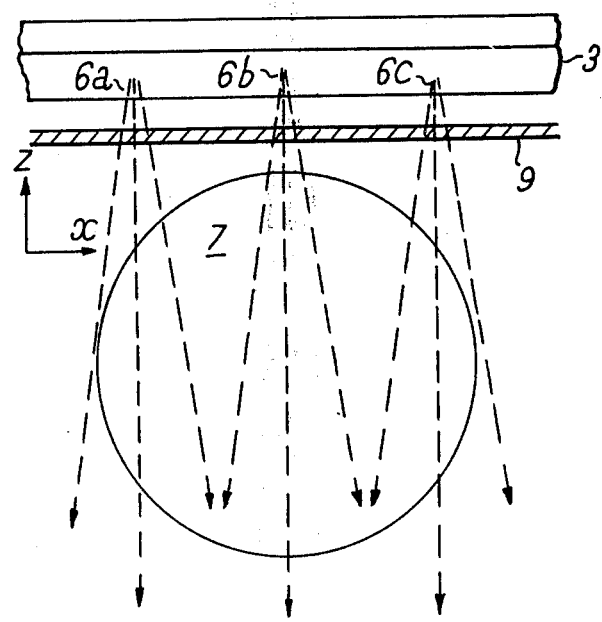
Figure 3:
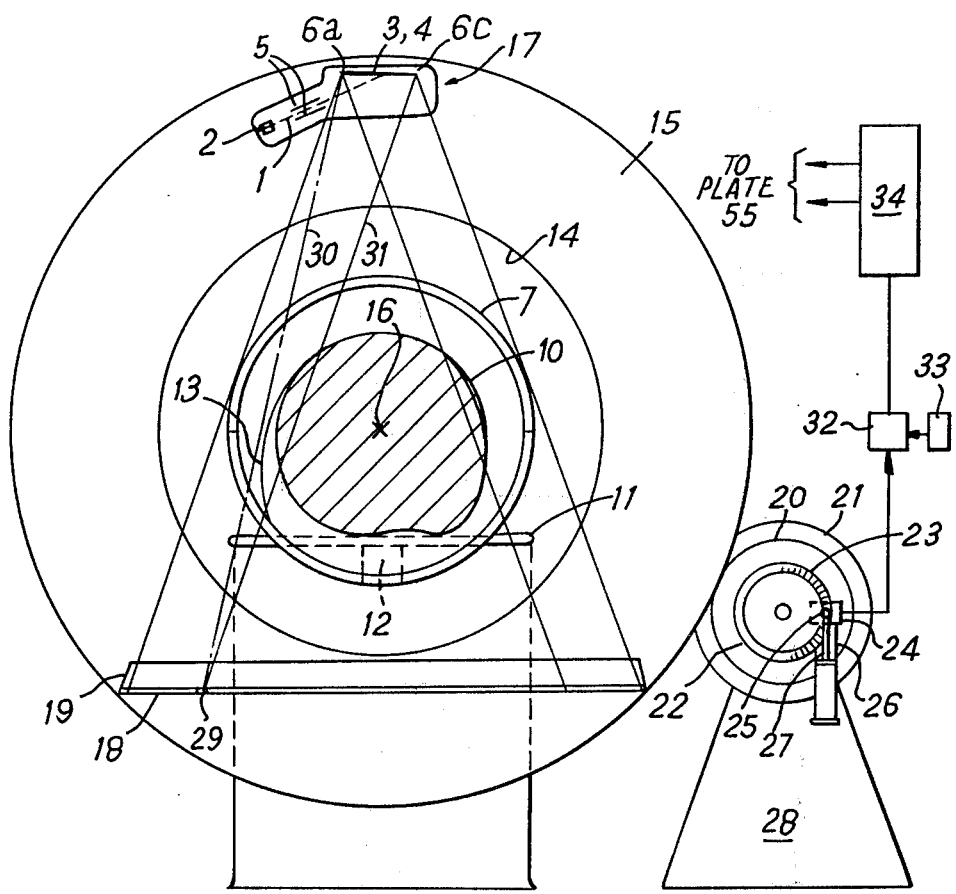

In order that the invention may be clearly understood and readily carried into effect one example thereof will now be described with reference to the accompanying drawings of which:

FIG. 1 shows, in simplified form, the essential features of an electrically scanned X-ray source for use with apparatus in accordance with the invention, FIG. 2 comprises FIGS. 2(a) and 2(b) which show in side and front view respectively, a collimating arrangement for use with the source of FIG. 1, and FIG. 3 shows a radiographic apparatus including an electronically scanned source of X-rays.

Referring now to FIG. 1, this shows only such elements of an X-ray tube as are necessary for the understanding of the invention. It will be appreciated that the tube envelope and other known features necessary to the operation of an X-ray tube have been omitted for the sake of clarity. A beam of electrons 1 is produced by an electron gun 2. The beam is suitably focussed and arranged to strike a target 3 at a single spot. Target 3, which may be made of tungsten, is inset into an anode member 4 which is at a suitable positive potential relative to gun 2. Anode member 4 may be made of copper and is cooled by means which are not shown in the Figure. The anode member and the target may be of a cross section similar to those of any suitable known X-ray source. However in the present invention they are of extended length in the direction indicated by $x$ in the drawings. Electron beam scanning means 5, which as shown comprise electrostatic deflection plates, but which could be of any other suitable type, are provided to scan the electron beam along target 3 in the $x$-direction to cause it to take up successive positions therealong, some of which are shown at 1$a$ 1$b$ and 1$c$. X-rays 6 are emitted from the target, at any point at which the electron beam strikes it, predominantly at an angle of about 50° to the electron beam, for X-rays produced by electrons of energy in the region of 10 kilo electron volts. Means, which will be further discussed hereinafter, are provided to restrict the X-rays, emitted from the source, substantially to the required direction, indicated by arrows 6, and those X-rays are allowed to leave the tube by means of a suitable window.

The linear scanning motion, required by the method of the above mentioned U.S. Pat. No. 778,614, is provided by arranging for the deflection means 5 to scan electron beam 1 along target 3 as appropriate. It will be appreciated that, if mechanical scanning of the detector is not to be necessary, an array of individual detectors, must be provided to cover the range scanned by the source. The source and detector array are, as previously described, rotated about a common axis in the y-direction.

A suitable collimating arrangement, for restricting the emitted X-rays to the desired region, is indicated in FIG. 2 which is related to FIG. 1 as shown by the co-ordinates x, y and z. The region in which the body to be examined is situated is indicated by reference numeral 7. The scanning of the X-ray beam in the x direction is indicated by 6a, 6b and 6c corresponding to 1a, 1b and 1c. The X-ray beam is restricted by a slit 8 in an absorbing shield 9 so that it does not irradiate in the y direction a region greater than the thickness of slice 7. Absorbing shield 9 may be provided in the wall of the X-ray tube if desired or may be internal or external to the tube. Slit 8 is of a length chosen to allow the desired range of scan. It will be appreciated that this collimating arrangement allows some spreading of the beams in the x direction, as indicated in the Figure. However, this fan-beam geometry may be compensated partly in the computations and partly by arranging for individual detectors to be sufficiently small and by providing further collimation of the individual beams at the detector array. Slit 8 may alternatively be replaced by a row of individual collimators. Furthermore, errors due to the angular distribution of energy in the fan beam of the X-ray system can be compensated in the computation of the map of absorption coefficients. For that purpose the system is first calibrated, i.e. the x-ray distribution is measured with known absorption between source and detectors.

The shape of the anode member 4 and target 3 may be chosen to suit any required application of a scanning X-ray source. Four example the shaping may be arranged to provide a fan shaped beam.

Referring now to FIG. 3, there is shown in front elevational view an apparatus including an electronically scanned source of X-rays. Features in FIG. 3 which are common to FIGS. 1 and 2 have been allocated the same reference numerals.

In FIG. 3, a body 10 to be examined is supported supine on a two-part couch 11, only the part of the couch 11 which is behind the apparatus as viewed is indicated in the drawing for reasons of clarity. The part of the body which is to be examined is surrounded by a two-part collar 7, which defines the region in which the body 10 is located. Collar 7 is made of material which is substantially transparent to X-radiation and a suitable material for the collar 7 is that known by the Registered Trade Mark "Perspex.38 The lower part of the collar 7 is secured to the couch 11 by way of a bracket 12, and the upper part of collar 7, which is removable from or hingedly secured to said lower part to permit ingress of the body 10, is fixedly secured to the said lower part once the body is in place.

Since in general the outline of the body 10 will not conform to the internal shape of the collar 7, a flexible bag 13 is wrapped around the body where it is surrounded by the collar and, once the collar parts have been fixedly secured together, the bag is inflated with water or another suitable liquid medium to prevent, so far as possible, the existence of air pockets between the collar 7 and the body 10.

The collar 7, and thus the part of the body which is of interest, is located in an aperture 14 in a turntable member 15 which is arranged to rotate around the collar 7 about an axis 16 which extends perpendicularly to the plane of the paper. The turntable member 15 carries an X-ray source 17, an array 18 of radiation detectors and a bank 19 of collimators associated therewith, and the member 15 and its attachments are rotated by means of a gear wheel 20 driven by an electric motor 21. The wheel 20 engages teeth (not shown) formed around the periphery of member 15. The detectors 18 can be of any suitable kind, for example scintillation crystals with associated photomultipliers, scintillation crystals with associated photodiodes etc.

The spindle of motor 21 carries a disc 22 which is formed with an annular graticule 23. The graticule co-operates with a photocell 24 and an associated light source 25 in a known manner to produce signal pulses which are indicative of the progress of the rotation of turntable member 15. Photocell 24 and the light source 25 are mounted on respective brackets 26 and 27 which are secured to a mounting frame 28 for the motor 21. It will be appreciated that the turntable member 15 will also require support and location and this is provided by a suitable frame which is not shown because it can take any suitable form and can easily be constructed by one skilled in the art. Moreover the form of the frame is not relevant to the understanding of this invention and to show it on the drawing would tend to obscure features which are relevant to such understanding.

The source 17 includes an elongated target / anode structure 3, 4, an electron gun 2 which produces a beam 1 of electrons and deflection plates 5, although deflection coils could equally well be used. Two extreme source positions 6a and 6c are shown in FIG. 3, from which it can be seen that, in any source position, a fan of radiation is directed at the body 10. It can also be seen that the detector array 18 takes no part in the lateral movement, this array being of sufficient breadth to accommodate the scanning of the radiation.

It will be appreciated that some detectors, for example that one shown at 29, need to be capable of receiving radiation from a number of different directions, for example as shown by the beams 30 and 31 which relate to source positions 6a and 6c respectively. The collimators in the bank 19 are arranged to allow for this.

The output signal pulses derived from the photocell 24 are applied to a timing pulse shaping circuit 32, which also receives start and stop command pulses from a remote control switch 33. The shaped pulses from circuit 32 are fed to a master timing circuit 34 which is arranged to generate deflection waveforms for application to the deflection plates 5 of tube 17 so that the lateral scanning of the radiation is synchronised with the rotation of turntable member 15. The arrangement is such that the electron beam 1 is scanned from 6a and 6c during the time in which the turntable member rotation through a small angle (say ½°) and then from 6c and 6a during the rotation of turntable 15 through the next ½°, the procedure being repeated until the total rotation achieved by member 15 has reached a desired amount.

The signals provided by the detector array 18 are processed in any convenient manner, such as that described in the aforementioned patent specification or that described in U.S. Pat. No. 3,924,129, allowance being made for the fact that the beam paths followed by the radiation through the body will not be strictly linear because of the effects of the steady rotation of turntable member 15.

To enable the invention to be adopted, apparatus similar to that shown in FIG. 3 may be used, except that the tube 17 is turned through 90° so that the target-/anode member 3, 4 lies perpendicular to the plane of the paper. In this case, unless the radiation emitted from the tube 17 is wide enough to encompass the whole area of collar 7 without the need for lateral scanning, the array of detectors is shortened so as to be commensurate with the spread of radiation produced by the tube 17 and then the tube 17 and the detector array 18 (with the collimator bank 19) are linked together and subjected to a mechanically driven lateral scanning motion.

The scanning of the electron beam 1 is then used to permit successive parallel slices of the body to be examined in sequence, and it will be appreciated that it is necessary to either displace the detector array 17 mechanically in a direction at right angles to the plane of the paper in FIG. 3 when the beam 1 is scanned, or to provide a plurality of banks of detectors for respective planes.

What I claim is:

1. Radiological apparatus comprising means defining a patient position, a source of X-radiation, a scanning frame supporting said source, so that the X-radiation projects through a substantially planar region of said patient position, drive means for causing said scanning frame, and with it said source, to execute an angular movement around the patient position, about an axis intersecting said region, so that the radiation projects through said region from a plurality of different directions, and detector means disposed to receive the radiation emergent from said patient position and to provide output signals indicative of the amount of radiation transmitted through said patient position along each of a plurality of paths in said region; the source comprising an X-ray emissive target which is elongated in a direction substantially parallel to said axis, a source of an electron beam, and deflecting means for deflecting said electron beam relative to said anode; means being provided for energising said deflecting means during the angular movement of said scanning frame so as to shift the region of impact of said electron beam along said anode and cause said radiation to be shifted so as to project through at least one further substantially planar region of said patient position; the detector means being adapted to accommodate the shift of said radiation and the drive means being adapted to cause said scanning frame to continue its angular movement with the electron beam in its deflected position.

2. Apparatus according to claim 1 wherein said source produces a substantially planar, fan-shaped spread of radiation and said detector means includes a plurality of detectors distributed across said spread.

3. Apparatus according to claim 2 including means for causing at least said source to execute lateral scanning movements, relative to said patient position, in the plane of said region.

4. Apparatus according to claim 1 wherein said detector means comprises a respective bank of detector devices for each of a number of positions of impingement of said electron beam on said elonagated anode.

5. Radiological apparatus including means defining a patient position, source means for projecting X-radiation through a substantially planar region of said patient position from each of a plurality of locations distributed angularly around said patient position, and detector means for detecting the radiation emergent from the patient position along a plurality of substantially co-planar paths, in said region from each of said locations, wherein said source means comprises a source of an electron beam, deflecting means for deflecting said beam in a direction substantially perpendicular to the plane of said paths, anode means for emitting said X-radiation in response to the impingement thereon of said electron beam and adapted to accommodate the deflection of said electron beam, and means for energising said deflection means to determine the location of said region within said patient position.

* * * * *